United States Patent [19]

Schoettley

[11] Patent Number: 4,634,429
[45] Date of Patent: Jan. 6, 1987

[54] SELF INJECTION APPLIANCE

[76] Inventor: Gerald L. Schoettley, 2640 McCord Rd., Toledo, Ohio 43615

[21] Appl. No.: 779,505

[22] Filed: Sep. 24, 1985

Related U.S. Application Data

[63] Continuation of Ser. No. 513,748, Jul. 15, 1983, abandoned.

[51] Int. Cl.$^4$ .............................................. A61M 5/00
[52] U.S. Cl. ..................................... 604/115; 24/563
[58] Field of Search ....... 604/115; 24/261 C, 262 GC

[56] References Cited

U.S. PATENT DOCUMENTS

| | | |
|---|---|---|
| 1,251,308 | 12/1917 | Wecht . |
| 2,234,961 | 3/1941 | Canada . |
| 2,704,071 | 3/1955 | Becker . |
| 2,757,665 | 8/1956 | Tanikawa . |
| 3,349,771 | 10/1967 | Baer . |
| 3,463,157 | 8/1969 | Hunt . |
| 3,760,803 | 9/1973 | Boothby . |
| 3,999,504 | 12/1976 | Kearse . |
| 4,195,636 | 4/1980 | Behnke . |
| 4,223,673 | 9/1980 | Harris . |
| 4,228,796 | 9/1980 | Gardiner . |

OTHER PUBLICATIONS

Harco Products, Inc., advertisement for "Hypo-Grip", *Diabetes Forecast*, Jul.-Aug. 1980.

Primary Examiner—Stephen C. Pellegrino
Attorney, Agent, or Firm—Emch, Schaffer Schaub & Porcello Co.

[57] ABSTRACT

A self-injection appliance is disclosed. The appliance is of one-piece construction having a guide portion, a platform and a non-symmetrical bight portion. The platform portion extends outwardly from the end of the guide portion and supports the fleshy portion of the users arm to facilitate self-injection.

5 Claims, 5 Drawing Figures

SELF INJECTION APPLIANCE

This is a continuation of co-pending application Ser. No. 513,748 filed on July 15, 1983 now abandoned.

BACKGROUND OF THE INVENTION

The present invention relates to a self injection appliance which is used by a person to inject, for example insulin, without the assistance of another person. The appliance specifically allows users of insulin or other prescription medications to use a hypodermic needle to self-inject themselves. It has been found that it is very difficult for an individual to self-inject himself in an arm without the use of the present appliance.

Attempts have been made in the past to design self-injection devices. Boothby, U.S. Pat. No. 3,760,803; Harris U.S. Pat. No. 4,223,673; Behnke U.S. Pat. No. 4,195,636 and Becker U.S. Pat. No. 2,704,071 are representative of such prior art attempts. Prior art devices have operated on a pinching principle. In each of the above-identified prior art devices, symmetrical jaws pinch the fleshy portion of the arm to project the flesh outwardly between the jaws. Such prior art devices are generally ineffective and uncomfortable.

The present appliance rather than pinching the flesh, rolls the flesh upon a platform portion of the appliance. It has been found that the present appliance is usable by persons of varying size and age with a greater degree of comfort.

SUMMARY OF THE INVENTION

The present appliance comprises a somewhat "C" shaped integral unit which includes a guide portion, an outwardly extending platform portion and an integrally connected bight portion between the guide portion and the platform portion. The bight portion is non-symmetrical. This allows the fleshy portion of the arm to be pushed upwardly onto the platform portion to facilitate self-injection.

BRIEF DESCRIPTION OF THE PREFERRED EMBODIMENT

Figure 5:
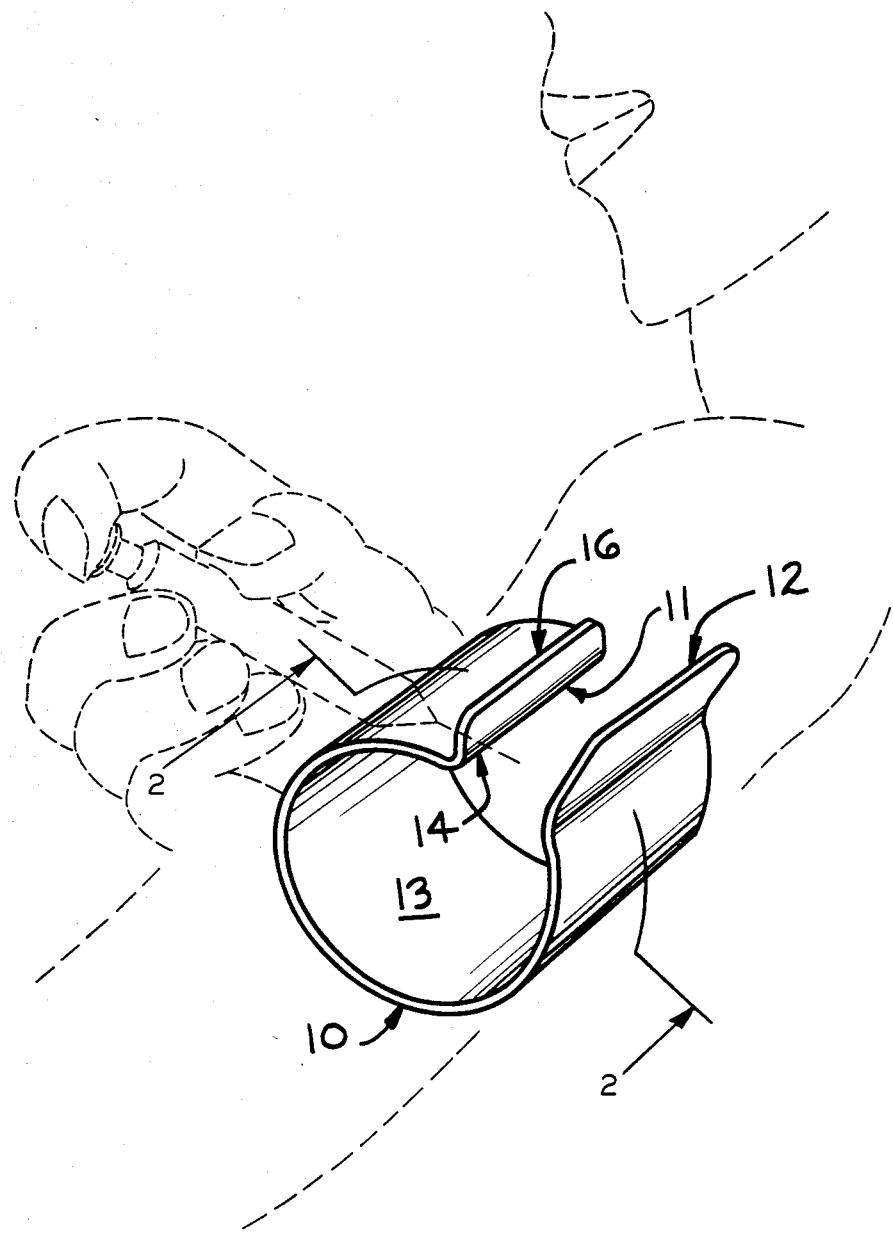
FIG. 5 is a perspective view of the self-injection appliance indicating in dashes a user of the appliance.

A self-injection appliance, according to the present invention, is indicated in the drawings by the reference number 10. The self-injection appliance 10 includes a guide portion 11, a platform portion 12 and a central or bight portion 13. The appliance 10 is of one-piece construction with the guide portion 11 and the platform portion 12 defining an opening 14 for receiving a users arm, as depicted in FIG. 5.

Preferably the appliance 10 is constructed from stainless steel, for example, AISI Type 410 steel which is resilient and has non-corrosive properties.

The appliance 10 is constructed of a single piece of stainless steel, heat treated for spring retention and polished to a smooth finish for comfort of the user.

In the present embodiment, the self-injection appliance 10 has a depth of approximately 2 and ¾ inches. However, this dimension may vary.

The bight portion 13 is integrally connected with the guide portion 11 and the platform portion 12. The guide portion 11 includes a rolled lip 16. The platform portion 12 extends outwardly from the rolled lip 16 of the guide portion 11.

Figure 1:
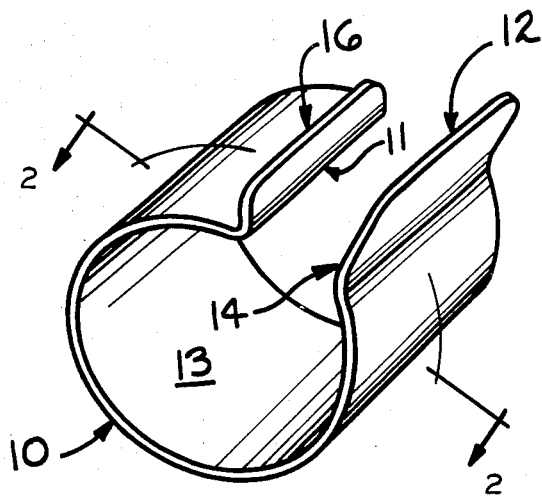
FIG. 1 is a perspective view of a self-injection appliance according to the present invention.
Figure 3:
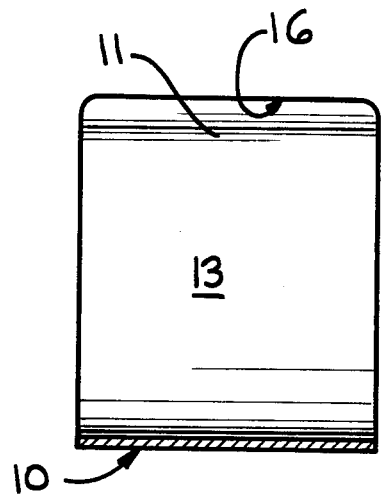
FIG. 3 is a cross-sectional view taken along the line 3—3 of FIG. 2.
Figure 2:
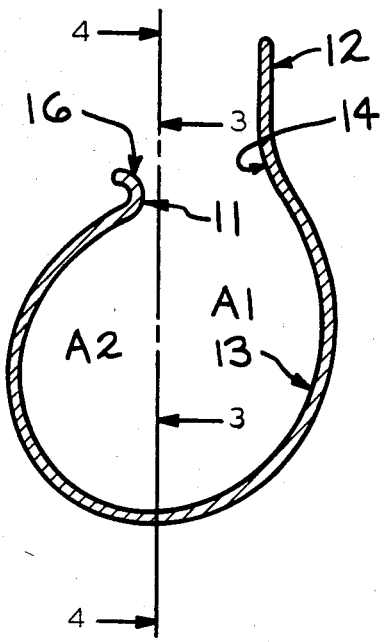
FIG. 2 is a cross-sectional view taken along the line 2—2 of FIG. 1.
Figure 4:
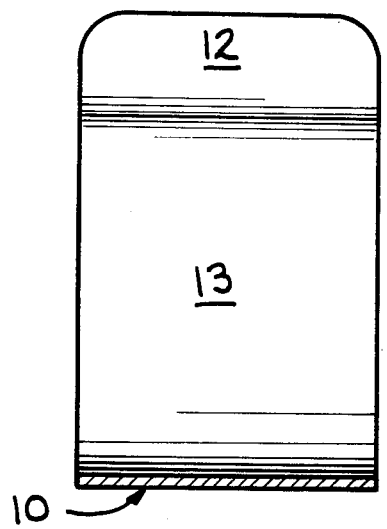
FIG. 4 is a cross-sectional view taken along the line 4—4 of FIG. 2.

As particularly shown in FIG. 2, the guide portion 11 is lower than the intersection of the bight portion 13 and the platform portion 12. Referring to FIG. 2, the bight portion 13 is non-circular and non-symmetrical. The bight portion 13 defines a large area A-1 adjacent the platform portion 12 as compared to the area A-2 adjacent the guide portion 11.

The design allows the appliance 10 to be used for either arm. Referring to FIG. 5, the appliance 10 is placed on the arm by turning the arm back and forth through the opening defined by the guide portion 11 and the platform portion 12. The arm is worked in by performing a back and forth motion of the arm while at the same time moving the appliance 10 in a forth and back motion. Once on the arm, the non-symmetrical contour of the appliance 10 allows movement of the flesh of the arm from the underside of the bicep upward. The guide portion 11, sitting lower in the flesh than the point at which the platform portion begins to extend from the bight portion, then further rolls the fleshy portion of the user's arm upward and against the platform portion 12, as shown in FIG. 5. The non-symmetrical contour of the appliance 10 allows movement of the flesh of the arm from the underside of the bicep upward to a position of the platform portion 10. Referring to FIG. 5, rather than pinching the fleshy portion of the user's arm between jaws, the fleshy portion of the arm is positioned on the platform portion 12 such that a hypodermic needle may be inserted above the guide portion 11 and into the fleshy portion of the arm which is resting against the platform portion 12.

Changes may be made in the above described preferred embodiment of the invention without departing from the spirit and scope of the following claims.

What I claim is:

1. A self-injection appliance made of spring steel comprising, in combination, a guide portion, a platform portion and a bight portion integrally connected between said guide portion and said platform portion, said guide portion and said platform portion being spaced from one another and defining an opening for receiving an arm, said arm being received through the opening defined by and against the guide and platform portions until the arm is fully through the opening, said bight portion being non-circular and non-symmetrical and said platform portion extending outwardly from said bight portion, said guide portion being lower than the intersection of the bight portion and the platform portion, said bight portion receiving said arm with the non-symmetrical contour of the bight portion engaging and moving the flesh of the arm upward against the platform portion whereby self-injection is facilitated and the fleshy portion of the arm is positioned on said platform portion to facilitate self-injection.

2. A self-injection appliance, according to claim 1, wherein said guide portion defines a free end and said guide portion includes a rolled lip at such free end.

3. A self-injection appliance according to claim 2, wherein said platform portion extends outwardly from said free end of said guide portion.

4. A self-injection appliance according to claim 2, wherein said appliance is constructed of stainless steel.

5. A self-injection appliance made of spring steel comprising, in combination:
   a guide portion, said guide portion defines a free end and said guide portion includes a rolled lip at such free end;
   a platform portion, said platform portion extending outwardly from said free end of said guide portion; and
   a bight portion integrally connected between said guide portion and said platform portion, said guide portion and said platform portion being spaced from one another and defining an opening for receiving an arm, said bight portion being non-circular and non-symmetrical and said guide portion being lower than the intersection of the bight portion and the platform portion, the non-symmetrical countour of the bight portion pushing against the underside of the bicep of the upper arm and the overlying flesh, the guide portion further lifting the fleshy portion up and rolling it against the platform portion whereby self-injection is facilitated.

* * * * *